(12) United States Patent
Sykes

(10) Patent No.: US 7,555,961 B2
(45) Date of Patent: Jul. 7, 2009

(54) TEST APPARATUS

(75) Inventor: Robert John Sykes, Essex (GB)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 11/569,136

(22) PCT Filed: May 5, 2005

(86) PCT No.: PCT/GB2005/001715

§ 371 (c)(1),
(2), (4) Date: Apr. 1, 2008

(87) PCT Pub. No.: WO2005/114722

PCT Pub. Date: Dec. 1, 2005

(65) Prior Publication Data

US 2008/0190212 A1 Aug. 14, 2008

(30) Foreign Application Priority Data

May 18, 2004 (GB) .................. 0411057.3

(51) Int. Cl.
*G01N 3/24* (2006.01)
(52) U.S. Cl. ....................................................... 73/841
(58) Field of Classification Search ............ 73/760–841
See application file for complete search history.

(56) References Cited

U.S. PATENT DOCUMENTS

| | | | |
|---|---|---|---|
| 5,641,913 A * | 6/1997 | Watanabe .................... | 73/827 |
| 6,078,387 A | 6/2000 | Sykes et al. | |
| 6,216,531 B1 * | 4/2001 | Zhou ......................... | 73/150 A |
| 6,341,530 B1 * | 1/2002 | Sykes ......................... | 73/831 |
| 6,564,115 B1 | 5/2003 | Kinnaird | |
| 2003/0067540 A1 | 4/2003 | Cox | |
| 2004/0103726 A1 * | 6/2004 | Cox ........................... | 73/842 |

FOREIGN PATENT DOCUMENTS

| EP | 0 772 036 | 5/1997 |
|---|---|---|
| JP | 61 168235 | 7/1986 |

OTHER PUBLICATIONS

Paul Walter; *Bond Testing Enters Mainstream PCB Assembly*; Microelectronics Journal; 1996; vol. 27, No. 1.
*Bond Testing Ultra fine Pitch Wirebonds* www.eurosemi.eu.com.
International Search Report for PCT Application No. PCT/GB2005/001715; Filed May 5, 2005; Date of Completion Jul. 14, 2005; Date of Mailing Jul. 26, 2005.

* cited by examiner

*Primary Examiner*—Max Noori
(74) *Attorney, Agent, or Firm*—Wood, Herron & Evans, L.L.P.

(57) ABSTRACT

A device (10) for shear testing of very small protrusions of an electrical semi-conductor device includes a sensor (30) for detecting surface contact of a shear test tool (15). The lateral shear force transducer is also used to detect scrubbing forces as the tool is reciprocated on the substrate, so as to give accurate surface contact sensing of non-rigid substrates. After contact sensing, the test tool is stepped back to ensure the shear test is performed without dragging of the tool on the substrate.

10 Claims, 2 Drawing Sheets

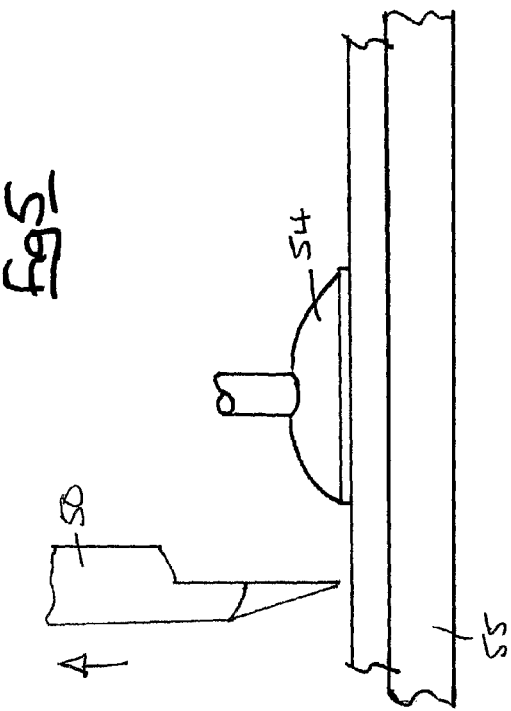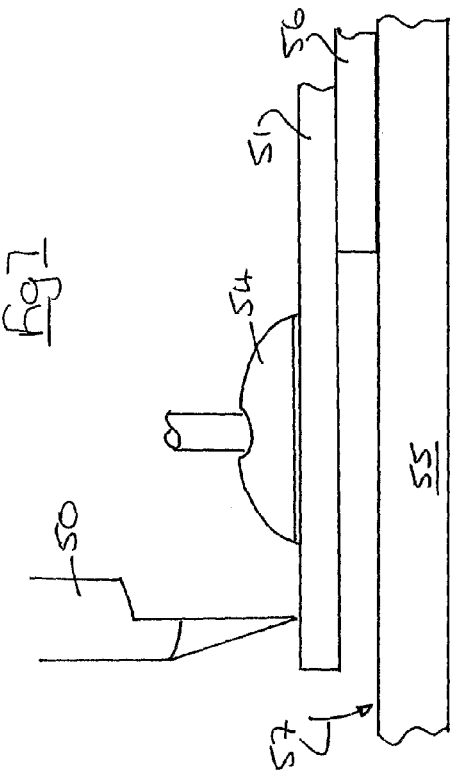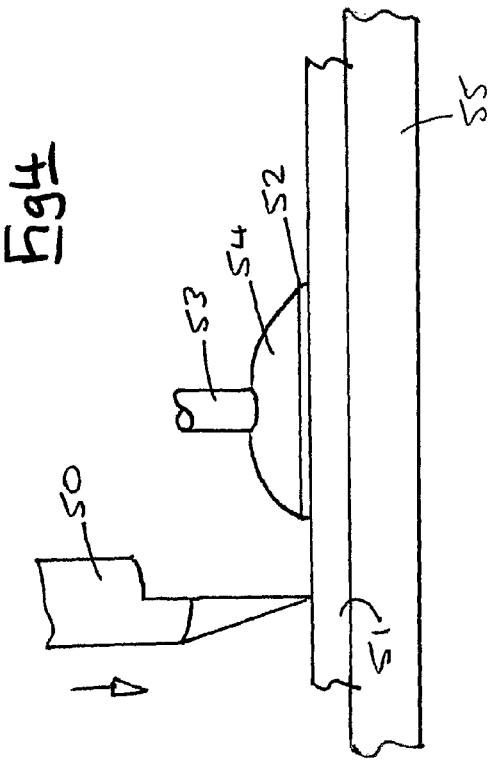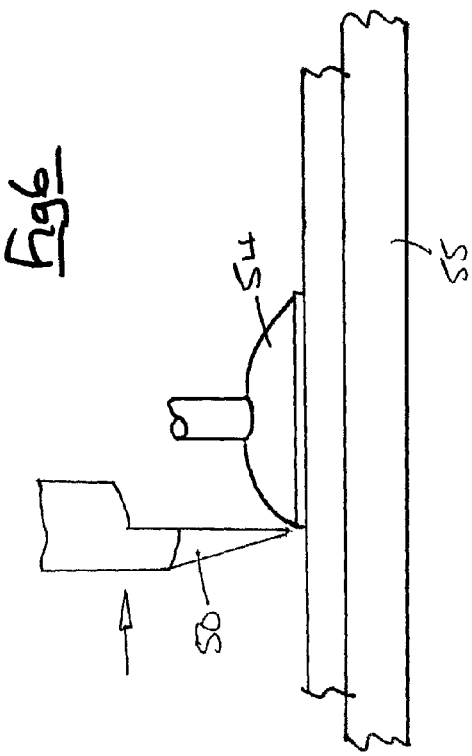

TEST APPARATUS

This invention concerns a device for testing the integrity of a bond between a semiconductor device and an electrical conductor thereof.

Semiconductor devices are very small, typically from 0.2 mm square to 15 mm square. Numerous sites for the bonding of electrical conductors are typically provided on the sense conductor substrate; these sites are typically about 0.05 mm wide and 0.05 mm to 0.7 mm apart. Each bond consists of a solder or gold ball adhered to the substrate. Very thin wires, usually about 0.025 mm in diameter, may be bonded to respective sites, and connect these sites to associated electrical circuitry and components. Alternatively the sites may bond directly to overlying components. It is necessary to test the bond integrity at the sites in order to gain confidence that the bonding method is adequate and that the bond strength is sufficient. Difficulties arise because of the very small dimensions of the components, the precision with which the testing device must be positioned, and the very small forces and deflections which are to be measured.

A known test apparatus has a probe for engagement with the bond at a respective site. The semiconductor device is restrained and the bond pushed sideways by the probe to determine the bond shear strength. A force transducer is incorporated in the device to measure the lateral force necessary to shear the bond.

In order to ensure repeatability it is essential for the probe to engage the side of the bond at a predetermined height above the surface of the semiconductor. This distance is small but critical since the bond is usually domed. A predetermined spacing from the surface both eliminates sliding friction from the probe on the semiconductor substrate, and ensures that the shear load is applied at a precise location in relation to the bond interface. Accordingly, in practice, the probe is moved into engagement with the semiconductor surface, and then withdrawn by a predetermined amount, typically 0.005 mm or less, before being moved sideways into contact with the bond site.

Several difficulties arise. Friction and stiction in the mechanism of the device itself may cause difficulties in sensing contact with the semiconductor surface; imprecise surface sensing will inevitably affect the distance by which the probe is withdrawn, and thus the height at which the bond is tested. The distances involved are very, very, small and thus every care needs to be taken to sense the exact moment of surface contact without compression of the semiconductor substrate. Care must also be taken to prevent uncontrolled movement of the probe at the test height, and prior to the application of the shear test force; such movement may again seriously affect the test result, and significant movement of the probe may damage an adjacent bond or wire.

The objectives of a low contact force when sensing the semiconductor substrate, and accurate control of test height are difficult to resolve.

U.S. Pat. No. 6,078,387 discloses a sensitive device for sensing contact of a test head with a substrate and adapted to immediately stop downward drive of the test head. The device ensures a relatively gentle touchdown on the substrate, and minimizes the small build-up of the touchdown load due to the delay between sensing contact with the substrate, and cessation of downward drive.

In use the test head is stepped back by a predetermined amount so as to have clearance above the substrate. This allows sideways movement of the test head so as to apply a shear force to the bond without dragging of the tool on the substrate.

More recently layered substrates have been proposed, and in which one layer protrudes to the side as a cantilever. Bonds are typically provided on the cantilevered portion, but current methods of contact sensing cannot prevent a very small degree of bending of the substrate. Accordingly it is very difficult to ensure that when the test head is stepped back, it is nevertheless clear of the substrate.

This difficulty is exacerbated because the local stiffness of the substrate may be unknown or difficult to calculate, for example in the region of a corner of the substrate, and consequently the required degree of step back is unknown.

The order of step back which is required is similar to the order of deflection, and accordingly a safe step back for all cases will result in an unacceptable variation in shear test height.

It is not desirable to calculate the required step back for cantilevered substrates, not least because the number of substrate variations is very large, and the substrate material is typically variable.

What is required is an apparatus and method adapted to sense contact on a non-rigid substrate, and yet to be capable of stepping back from the substrate to a predetermined clearance, notwithstanding that the substrate surface moves as the contact force is reduced.

According to one aspect of the invention there is provided a shear test device having a test head adapted to be driven substantially perpendicularly towards and away from a substrate and including sensing means for sensing contact of the test head with the substrate, the test head being further adapted to be driven transversely over the substrate in order to apply a shear load to a protrusion on the substrate, and including measurement means for sensing the shear force applied to the protrusion, wherein said measurement means is further adapted to detect a dragging load of the test head on the substrate.

Preferably the sensing means comprise a displacement detector which in the preferred embodiment is an opto-electronic sensor adapted to cease movement of said test head. Optical detection ensures friction free sensing of the substrate surface.

In a preferred embodiment the device further includes a driver to transversely reciprocate the test head over the substrate, thereby to permit detection of a dragging load.

According to another aspect the invention provides a method of shear testing protrusions of a substrate, and comprising the steps of:
 a) advancing a test tool to the substrate,
 b) ceasing advance of the test tool on contact with the substrate,
 c) withdrawing the test tool by a predetermined distance,
 d) transversely reciprocating the test tool with respect to the substrate, and detecting any dragging force,
 e) if a dragging force is detected, further withdrawing the test tool by a fraction of said predetermined distance and repeating step d) until no dragging force is detected, and
 f) moving said test tool laterally against a protrusion of the substrate to conduct a shear test.

The method may further comprise the additional steps of:
 e1) if no dragging force is detected, advancing said test tool by a fraction of said predetermined distance and repeating step d) until a dragging force is detected, and
 e2) withdrawing said test tool by a fraction of said predetermined distance before conducting said shear test.

This 'scrubbing' action permits highly accurate sensing of the substrate surface, even if the surface is somewhat flexible. Most importantly surface contact is sensed by the existing lateral force sensor, rather than by a vertical force sensor.

Reciprocation should ideally bring the test tool back to the contact location, or substantially to the contact location.

The method optionally includes the step of withdrawing said test tool by a set distance after sensing dragging, so ensuring a significant but accurate pre-set shear test height.

Other features of the invention will be apparent from the following description of a preferred embodiment, illustrated by way of example only with reference to the accompanying drawings in which:—

Figure 2:
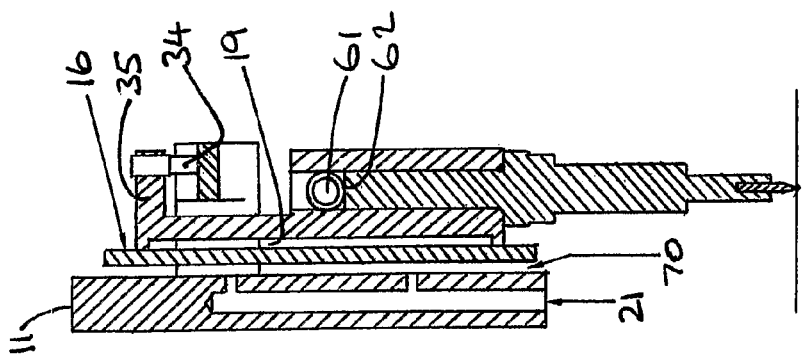
FIG. 2 is a section on line X-X of FIG. 1 illustrating the passive condition.
Figure 3:
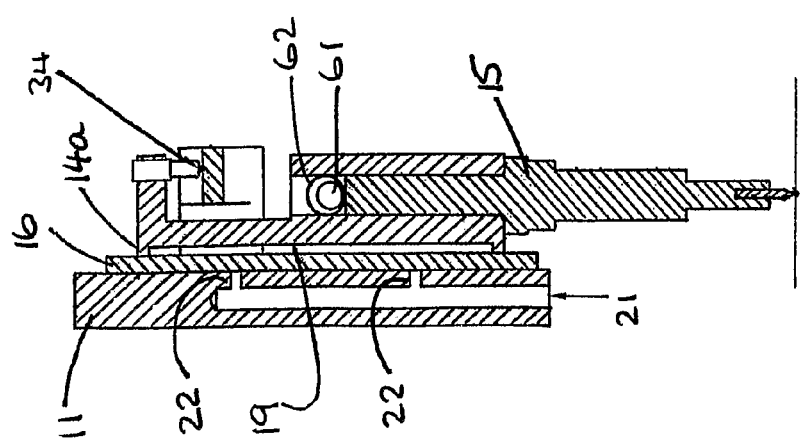

FIG. 3 corresponds of FIG. 2 and shows the active condition.

FIGS. 4-6 illustrate stages in the movement of the device, on an enlarged scale.

FIG. 7 illustrates a cantilevered substrate.

Figure 1:
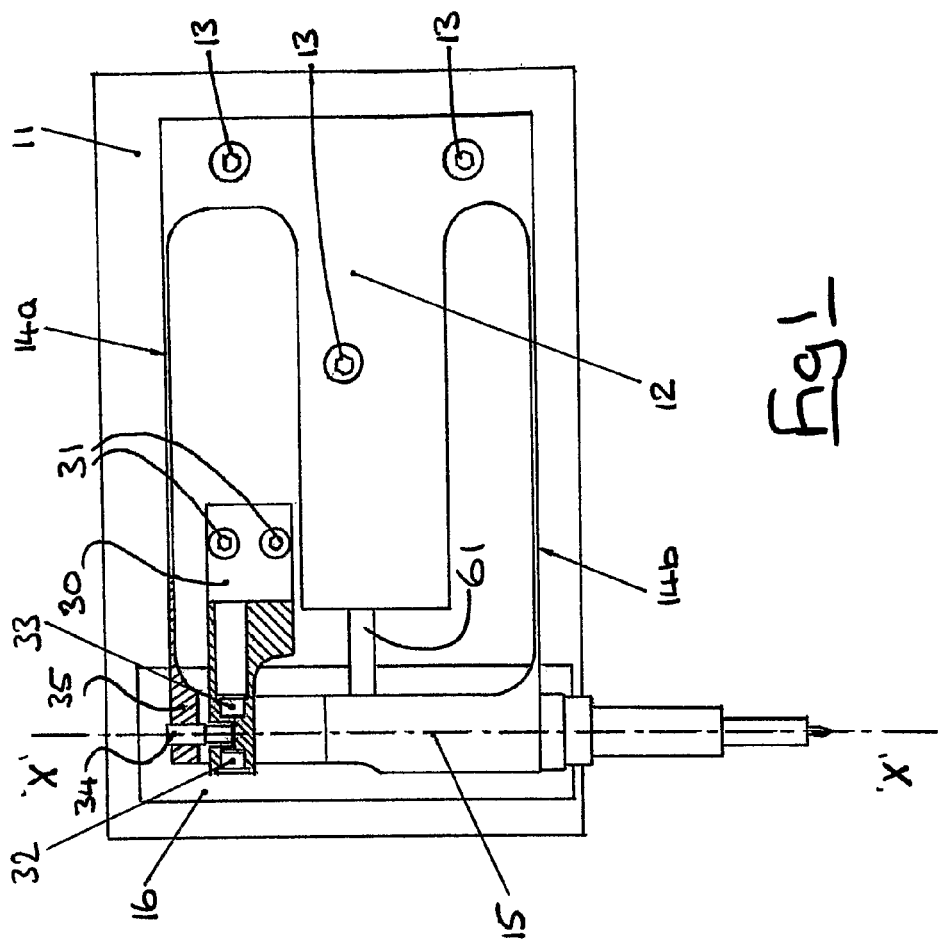
FIG. 1 is a side elevation for a prior device for contact sensing.

With reference to FIGS. 1-3, a transducer cartridge 10 comprises a base plate 11 to which is rigidly attached a fixed mass 12 by screws 13. The fixed mass has upper and lower cantilever arms 14a,14b to the free ends of which are attached a moving mass 15. The cantilever arms 14a,14b permit up and down movement of the moving mass 15, and together determine the rest position of the moving mass 15.

The inner sides of the free ends of the arms 14a,14b carry a bearing plate 16 which itself lies against the base plate 11. In the rest position the arms 14a,14b are arranged to exert a bias force towards the base plate 11 which is just sufficient to clamp the bearing plate 16 and thus prevent oscillation of the moving mass 15 in the up and down direction. This bias force ensures that the moving mass 15 does not move relative to the base plate 11 whilst the base plate is itself being moved.

The base plate 11 includes air bearing 20 comprising an air supply duct 21 having outlet ports 22 to a chamber 19 on the underside of the bearing plate 16. The supply of air under pressure to the duct 21 causes the bearing plate 16 to move away from the base plate 11, against the bias force of the arms 14a,14b, and thus permits friction free movement of the moving mass in the up and down direction.

The bias force and the degree of air pressure required to overcome it is a matter of detailed design, and can be determined by the skilled man according to the test requirements. Likewise, the area of engagement of the arms 14a,14b on the bearing plate 16, the area of engagement of the bearing plate 16 on the base plate 11, the air porting arrangement and other variable factors may be determined according to particular circumstances. Generally speaking the bias force should be just sufficient to restrain movement of the moving mass 15 whilst performing a test, and the air pressure should be just sufficient to allow the moving mass 15 to move freely.

A travel sensor mount 30 is fixed to base plate 11 by screws 31. The mount 30 has a photoelectric emitter 32 and receiver 33 between which extends a stud 34 which is screw-threaded in a projection 35 of the upper cantilever arm 14a. As illustrated in FIG. 1, the stud 34 can be screwed into engagement with the mount 30 and thereby jack the moving mass 15 upwards relative to the base plate 11. This arrangement permits an adjustment of the proportion of the actual mass of the moving mass 15 which is carried the arms 14a,14b and which is carried by the stud 34, when the air bearing is active. This ensures that the lightest of contacts by the probe tip causes slight upward movement of the probe, and thereby changes the degree with which the stud 34 obscures the light path between emitter 32 and receiver 33. Typically the initial contact force of the probe tip is in the range 0-50 g, for example 15 g, but can be adjusted according to the projection of the stud 34.

This load sharing arrangement alleviates the problem that the actual mass of the moving mass 15 may be sufficient to indent or deflect the surface 40 of the semiconductor 41 or that the apparatus moving the probe into contact with the surface 40 may embed the probe in the surface before downwards drive ceases. Inevitably there is a small but finite time for the contact to be sensed, and for the Z axis drive to stop. The present arrangement allows the point of contact to be sensed with considerable precision since movement of the moving mass 15 is free of friction and the photoelectric sensor 32,33 can detect small changes in the degree of light transmitted. The time taken for the Z axis drive to stop can be related to a precise distance, and consequently an allowance can readily be made in the distance through which the probe is withdrawn prior to test.

A projection 61 of the base plate is loosely located in an aperture 62 of the test head, and serves to restrict movement of the arms 14a,14b to their elastic range.

Stages of use of the device are illustrated in FIGS. 4-6 which show a probe tip 50, semiconductor substrate 51, electrical contact 52, electrical wire 53 and bond 54.

The precise shape of the bond 54 may vary due to production techniques, and consequently the bond shown in FIGS. 4-7 is for illustration purposes only. Some dimensions are exaggerated in order to show features more clearly.

In use air pressure is applied and the moving mass is supported by elastic deflection of the arms 14,14b. At this stage the proportion of the load taken by the stud 34 can be adjusted to give the desired touch down load. It should not be necessary to adjust the stud after initial setting unless test conditions are changed. Then, the back plate 11 is driven towards the substrate 51 until the probe tip 51 is close to the test site; the actual mass of the moving mass 15 is not so great as to oscillate under rapid movement of the base plate.

Just above the substrate movement of the back plate is slowed until contact is sensed by the optical sensors 32,33 (FIG. 4). The gap 70 created at the air bearing is exaggerated in FIG. 3; in practice air pressure will be selected to ensure that the arms 14a,14b just separate from the back plate 11.

Once contact is sensed, travel of the back plate ceases. The air supply to the bearing also ceases, and as a consequence the beams move imperceptibly to engage the back plate (FIG. 2). At this stage the moving mass 15 is held firmly relative to the back plate by the inherent sideways spring force generated by the beams 14a,14b. Slight residual load in the beams 14a,14b may also be retained by this inherent spring force. Movement due to ceasing of the air supply is solely in the direction of the collapsing air gap, and the probe tip maintains light contact with the substrate surface.

The back plate is then retracted by a predetermined amount (FIG. 5) and moved laterally against the bond (FIG. 6) to commence the shear test.

In practice drive of the back plate is automated to ensure repeatability of test conditions. Positioning of the probe in the vicinity of a bond to be tested is typically carried out manually using magnifying techniques, or by pre-programming if a datum and bond site spacing are known.

Several different test heads may be provided, each designed according to the range of applied loads. Typically test heads adapted to apply nominal loads of 25 g, 250 g, 5 kg and 100 kg may be provided.

The apparatus has no internal moving parts and indeterminate friction and stiction forces are eliminated.

As illustrated in FIG. 7, a problem arises if the substrate is deformable. FIGS. 4-6 assume that the substrate 51 is on a firm supporting surface 55. If however the substrate 51 is cantilevered from another device 56 there will be inevitable bending in the direction of arrow 57, as the probe tip touches down. As a consequence, the vertical step back of the probe tip 50 may be insufficient to ensure clearance when the substrate has been restored to its initial position by inherent resilience thereof. In such circumstances the probe tip will be closer to the substrate 51 just prior to the shear test, or will be in light dragging contact therewith notwithstanding that vertical load on the probe tip is almost zero. In the former case, the test result will not be comparable because of different test height, and in the latter case the dragging force will mask the shear load recorded.

According to the invention, any force sensed by lateral movement of the probe tip are assumed to be due to dragging on the substrate. In such circumstances the tip is stepped up by a suitably small amount, typically 0.5 µm, and lateral movement recommenced. If force is sensed, the tip is again stepped up, and so on until lateral movement is force free, at which point the shear test is performed. Lateral movement of the tip by about 10 µm is sufficient to indicate dragging.

This method of operation allows existing test apparatus to be adapted to more flexible substrates whilst avoiding the need for sensitive force measurement in the vertical direction. Friction free optical contact sensing is retained.

In order to improve test height accuracy, a scrub test may be performed. Such a test is useful in case of supported and unsupported substrates, or where the substrate material is flexible or easily indented.

In this embodiment the probe tip is advanced into contact with the substrate, and surface contact is sensed as previously described in relation to FIG. 4. The tool tip is then stepped back by the standard amount, and moved laterally to see if lateral force is detected. An iterative process is then adopted to ensure detection of forces within a predetermined range indicative of light intimate contact between probe tip and substrate. If no force is detected the probe is advanced, and if force is detected the probe is withdrawn, typically by a very small distance in the region of 5 µm. Such an arrangement gives a highly accurate indication of tip position relative to substrate surface, and irrespective of substrate resilience. As a consequence step-up of the tip prior to shear testing gives a highly accurate test height, and test repeatability is improved.

The invention claimed is:

1. A shear test device comprising:
   a test head adapted to be driven substantially perpendicularly towards and away from a substrate, the test head being further adapted to be driven transversely over the substrate in order to apply a shear load to a protrusion on the substrate;
   a sensor operative to sense contact of the test head with the substrate;
   a force transducer operative to measure the shear force applied to the protrusion, wherein said force transducer is further operative to detect a dragging load of the test head on the substrate prior to application of the shear load to the protrusion; and
   a driver operative to transversely reciprocate said test head.

2. A device according to claim 1 wherein said sensor comprises a displacement detector.

3. A device according to claim 2 wherein said detector is an opto-electronic sensor.

4. A device according to claim 2 and further including a control operative to cease transverse movement of the test head on detection of a predetermined dragging load by said force transducer.

5. A method of shear testing protrusions of a substrate, and comprising:
   a) advancing a test tool to the substrate,
   b) ceasing advance of the test tool on contact with the substrate,
   c) withdrawing the test tool by a predetermined distance,
   d) transversely reciprocating the test tool with respect to the substrate, and detecting any dragging force prior to contact with a protrusion,
   e) if a dragging force is detected, further withdrawing the test tool by a fraction of said predetermined distance and repeating step d) until no dragging force is detected, and
   f) moving said test tool laterally against the protrusion of the substrate to conduct a shear test.

6. The method of claim 5 and further comprising the additional steps of:
   e1) if no dragging force is detected, advancing said test tool by a fraction of said predetermined distance and repeating step d) until a dragging force is detected, and
   e2) withdrawing said test tool by a fraction of said predetermined distance before conducting said shear test.

7. The method of claim 5 and including the alternative step of withdrawing said test tool by a set distance after first sensing dragging and immediately conducting said shear test.

8. A device according to claim 3 and further including a control operative to cease transverse movement of the test head on detection of a predetermined dragging load by said force transducer.

9. The method of claim 6, further comprising:
   withdrawing said test tool by a set distance after first sensing dragging and immediately conducting said shear test.

10. A shear test device comprising:
    a test head adapted to be driven substantially perpendicularly towards and away from a substrate, the test head being further adapted to be driven transversely over the substrate in order to apply a shear load to a protrusion on the substrate;
    a sensor operative to sense contact of the test head with the substrate;
    a force transducer operative to measure the shear force applied to the protrusion, wherein said force transducer is further operative to detect a dragging load of the test head on the substrate prior to application of the shear load to the protrusion;
    a control operative to cease transverse movement thereof on detection of the dragging load by said force transducer; and
    a driver operative to transversely reciprocate said test head.

* * * * *

UNITED STATES PATENT AND TRADEMARK OFFICE
CERTIFICATE OF CORRECTION

| | | |
|---|---|---|
| PATENT NO. | : 7,555,961 B2 | Page 1 of 1 |
| APPLICATION NO. | : 11/569136 | |
| DATED | : July 7, 2009 | |
| INVENTOR(S) | : Robert John Sykes | |

It is certified that error appears in the above-identified patent and that said Letters Patent is hereby corrected as shown below:

On the Title Page

At (73), change "Nordson Corporation, Westlake, OH" to --Dage Precision Industries, Ltd., Buckinghamshire, United Kingdom--.

Signed and Sealed this
Eighth Day of March, 2011

David J. Kappos
*Director of the United States Patent and Trademark Office*